United States Patent [19]

Kokubo et al.

[11] Patent Number: 5,372,998
[45] Date of Patent: Dec. 13, 1994

[54] POWDERY MATERIAL FOR PREPARING DRUG-COATING SOLUTION

[75] Inventors: Hiroyasu Kokubo, Joetsu; Yuichi Nishiyama, Kubiki; Hiroaki Muto, Tokyo, all of Japan

[73] Assignee: Shin-Etsu Chemical Co., Ltd., Japan

[21] Appl. No.: 31,347

[22] Filed: Mar. 12, 1993

[30] Foreign Application Priority Data

Mar. 23, 1992 [JP] Japan .................. 4-064477

[51] Int. Cl.$^5$ ............................................ A01N 43/04
[52] U.S. Cl. .................................... 514/57; 424/490; 424/480; 424/468
[58] Field of Search ............... 514/57, 781; 424/35, 424/490, 468, 480

[56] References Cited

U.S. PATENT DOCUMENTS

| | | | |
|---|---|---|---|
| 3,907,983 | 9/1975 | Seth | 424/35 |
| 5,017,383 | 5/1991 | Ozawa | 424/490 |
| 5,093,200 | 3/1992 | Watanabe | 424/468 |

Primary Examiner—Thurman K. Page
Assistant Examiner—William E. Benston, Jr.
Attorney, Agent, or Firm—Parkhurst, Wendel & Rossi

[57] ABSTRACT

The present invention provides a powdery starting material for preparing a drug-coating solution, which has high safety as a drug component and is very rapidly dissolved in room temperature water upon preparation of a coating solution. The powdery starting material for preparing a drug-coating solution comprises hydroxypropylmethyl cellulose and/or methyl cellulose particles having an average particle size ranging from 200 to 1000 μm and whose content of particles having a particle size of 75 μm or smaller is not more than 30% by weight. More preferably, the viscosity of a 2% by weight aqueous solution of the powdery starting material as determined at room temperature ranges from 2 to 60 cP and preferably 2 to 20 cP.

5 Claims, No Drawings

POWDERY MATERIAL FOR PREPARING DRUG-COATING SOLUTION

BACKGROUND OF THE INVENTION

The present invention relates to a powdery material for the preparation of a drug-coating solution which is used for coating the surface of, for instance, medicinal tablets in order to suppress the bitterness thereof.

The surfaces of medicinal tablets having a bitter taste are frequently coated with a water-soluble film for the purpose of making the administration thereof easy. Hydroxypropylmethyl cellulose has most widely been used as a material for such film coating. In addition, methyl cellulose has likewise been used.

A coating solution obtained by dissolving a powdery material as a starting material is used for coating tablets with films. In the early 1950s when the technique for coating the surface of medicinal tablets was developed, a coating solution was prepared by dissolving starting particles for film-coating in an organic solvent. For instance, the material for film-coating was once dispersed in a poor solvent and then the resulting dispersion was mixed with a good solvent to give a coating solution. This method permitted the preparation of a uniform solution within a short period of time. Water has been used instead of organic solvents for reducing the cost required for coating and for the requirement of environmental protection since the early 1970s. However, the use of water as a solvent requires time-consuming and complicated operations such as heating and cooling operations in the preparation of a coating solution. If a powdery material such as hydroxypropylmethyl cellulose is directly introduced into water being at room temperature, the material forms large agglomerates in water and the dissolution of such agglomerates requires a long time period on the order of several hours to one day. For this reason, particles of, for instance, hydroxypropylmethyl cellulose are, in fact, dispersed in hot water in advance and then the resulting dispersion is cooled to room temperature. However, it takes about several hours to obtain a uniform solution even when the resulting hot solution is cooled with cold water.

Since the improvement of production efficiency can be ensured by substantially reducing the time required for the preparation of a coating solution, there has been adopted a method in which a material for film-coating is introduced into water on the day before the practical use thereof and kept to stand over night. If it is planned to perform a film-coating process after the end of consecutive holidays, the preparation of a coating solution is started before the consecutive holidays and allowed to stand over 2 to 3 days. Any preservative cannot be added to coating solutions since any drug cannot include such a substance and, therefore, the coating solution is putrefied while storing it and cannot be used in the worst case.

Ideally speaking, a coating solution is thus prepared immediately before the practical use in order to prevent any decay of the solution prepared. To prepare a coating solution immediately before the practical use, a homomixer is in general used. However, this practice suffers from various problems. For instance, too much expenses are required, a large amount of foam is formed depending on the conditions for dissolution and it takes, instead, a long time for completely removing the foam.

An agent for promoting dissolution of a starting material may be used to prepare a coating solution ready for use without using any machinery. Some starting materials such as hydroxypropylmethyl cellulose can be commercially available in the form of, for instance, solution type and powder type premixes which are previously admixed with additives such as pigments, plasticizers and surfactants. These additives previously added to these starting materials have the effect of promoting the dissolution of the starting materials and thus the solution type premixes can be used as such or after being diluted with water. Examples of such premixes commercially available include Opadry available from Colorcon Company which is powder type one and has widely been used. A plasticizer such as polyethylene glycol (PEG) having a surface active effect is inevitably incorporated into the premixes of powder type to improve the dispersibility thereof. The powdery premix permits the immediate preparation of a coating solution by the use of water at room temperature as disclosed in Japanese Paten,: Application Publication No. 2-29655. However, these additives may possibly affect the stability of medicinal substances to be coated with the resulting coating solution and may lead to an increase in its cost.

Under such circumstances, there has been desired the development of a powdery starting material for preparing a solution used in coating of medicinal tablets that does not require the use of any particular machinery and the addition of any other additive and that ensures high medical safety and a high dissolving rate.

SUMMARY OF THE INVENTION

The present invention has been developed to solving the foregoing problems associated with the conventional methods and it is an object of the present invention to provide a powdery starting material for preparing a drug-coating solution that is highly safe from the viewpoint of medicine and that can very quickly be dissolved in water of room temperature.

According to the present invention, the foregoing object can effectively be accomplished by providing a powdery starting material for preparing a drug-coating solution comprising hydroxypropylmethyl cellulose and/or methyl cellulose particles having an average particle size ranging from 200 to 1000 $\mu$m and whose content of particles having a particle size of 75 $\mu$m or smaller is not more than 30% by weight.

The starting particles according to the present invention have a large particle size such that they do not cause agglomeration even if they are added to water having room temperature and individual particles have a large surface area sufficient for allowing rapid dissolution in water. Thus, the powdery starting material according to the present invention can rapidly be dissolved in water of room temperature.

It has conventionally been inevitable to use a specifically designed device or a premix that contains additives such as a plasticizer and a surfactant in order to achieve rapid dissolution of a coating material in water. For this reason, a coating solution cannot satisfactorily be prepared immediately before the practical use depending on the installations and preparations and the safety of the resulting coated drugs may adversely be affected. The powdery starting material according to the present invention can completely solve the foregoing problems associated with the conventional methods.

DETAILED EXPLANATION OF THE INVENTION

Examples of particles used for preparing the powdery starting material according to the present invention include hydroxypropylmethyl cellulose and methyl cellulose which may be used alone or in combination. Among these, particles of hydroxypropylmethyl cellulose are particularly preferred. In these compounds, the hydrogen atoms of the hydroxyl groups on the cellulose moieties are partially or completely substituted with hydroxypropylmethyl groups or methyl groups.

The average particle size of these particles ranges from 200 to 1000 $\mu$m. This is because if it is less than 200 $\mu$m, the particles cause agglomeration upon being dispersed in water to give a coating solution and require a long time period till a dispersed state which ensures complete dissolution is obtained. On the other hand, if it exceeds 1000 $\mu$m, the surface area per unit weight is small and it takes a long time period till each particle disappears through complete dissolution.

The content of particles having a particle size of not more than 75 $\mu$m should be limited to not more than 30% by weight on the basis of the total weight of the powdery starting material. If the content thereof exceeds 30% by weight, the probability that the powdery material causes agglomeration would be high even if the average particle size of the material is not less than 200 $\mu$m and this leads to substantial increase of the time required for complete dissolution thereof in water.

These particles of hydroxylpropylmethyl cellulose and/or methyl cellulose are used in the form of a solution in water. The viscosity of the resulting aqueous solution thereof ranges from 2 to 60 cP and preferably 2 to 20 cP as determined at room temperature and a concentration of 2% by weight. This is because if the viscosity of the aqueous solution exceeds 60 cP, the concentration of the solution must be extremely low when it is practically used for coating on the surface of, for instance, medicinal tablets through spray-coating. The concentration of the coating solution practically used is in general adjusted to 3 to 12% by weight. The use of an extremely low concentration of the coating solution is not practical since a long time is required for drying the coated film.

The size of particles of hydroxypropylmethyl cellulose and methyl cellulose may be controlled by, for instance, a method for growing particles having a predetermined particle size starting from fine particles or solutions of these compounds and a method comprising pulverizing a massive body thereof and then classifying the resulting pulverized particles.

Examples of methods for growing particles having a predetermined particle size include stirred granulation methods, stirred fluidized bed granulation methods, fluidized bed granulation methods, spray dry methods and spray dry fluidized bed granulation methods.

The stirred granulation method comprises adding a small amount of water to commercially available powdery hydroxypropylmethyl cellulose having an average particle size of about 50 $\mu$m with stirring to cause agglomeration and to thus increase the particle size thereof and then drying. In the stirred fluidized bed granulation method or the fluidized bed granulation method, water is sprayed on moving particles for granulation. The particle size of the resulting granulated particles may easily be controlled by changing the amount of water added or sprayed and conditions for the granulation operation. The spray dry method comprises once dissolving a coating material in water, spraying the resulting aqueous solution and drying the liquid particles thus formed. In this case, the particle size can be controlled by properly changing the concentration of the aqueous solution to be sprayed and conditions for spraying. The spray dry fluidized bed granulation method comprises once forming fine particles through spray drying and simultaneously granulating with the same solution. The spray feed of the solution permits an increase of the particle size.

All of these methods permit the preparation of particles having a predetermined particle size, but the particle size distribution and bulk density of the resulting particles vary depending on the methods selected. The spray dry methods and the spray dry fluidized bed granulation methods are preferred for the preparation of particles which are uniform in their particle size. Alternatively, the stirred granulation methods and the stirred fluidized bed granulation methods are preferred for the preparation of powdery products having a high bulk density.

The method comprising pulverizing a massive body and then classifying the resulting particulate product comprises appropriate combination of various pulverization conditions and selection of the mesh size of a sieve used.

The starting particles according to the present invention have a large particle size such that they do not cause agglomeration even if they are charged in water having room temperature and individual particles have a large surface area per unit weight of the particles sufficient for allowing rapid dissolution in water.

The present invention will hereinafter be explained in more detail with reference to the following non-limitative working Examples.

EXAMPLES 1 TO 3

Samples of hydroxypropylmethyl cellulose (coating materials) were pulverized into particulate products having particle size distribution as listed in the following Table 1. An amount of 188 ml of purified water was introduced into a bottle of 8 ounces provided with a stirring blade and the bottle as such was immersed in a thermostatic chamber maintained at a temperature of 25° C. The foregoing pulverized sample of hydroxypropylmethyl cellulose (12 g) was, at a time, added to the purified water at an instance when the temperature of the purified water in the bottle was equilibrated at 25° C., while stirring it at a velocity of 500 rpm. The stirring was continued until the sample was completely dissolved.

The dissolution of the particles was continuously monitored and the solution was passed through a sieve of 18 mesh (850 $\mu$m) after undissolved particles or agglomerated masses disappeared. It was confirmed whether or not residual particles were present on the sieve and there was recorded the time required for complete dissolution of the particles after the addition thereon to the purified water as the dissolution time. The results thus obtained are listed in Table 1.

EXAMPLE 4

The same procedures used in Example 1 were repeated except that methyl cellulose pulverized into particles having a particle size shown in Table 1 was substituted for the hydroxypropylmethyl cellulose used in Example 1.

EXAMPLES 5 TO 7

The same procedures used in Example 1 were repeated except that commercially available hydroxypropylmethyl cellulose which was treated by granulation through spraying water thereon according to the stirred fluidized bed granulation method to give particles having a particle size distribution shown in Table 1 was used. The results are summarized in Table 1.

COMPARATIVE EXAMPLES 1 TO 3

The same procedures used in Example 1 were repeated except that commercially available hydroxypropylmethyl celluloses per se were used. The results obtained are listed in Table 1 together with the particle size distribution of the celluloses.

COMPARATIVE EXAMPLE 4

The same procedures used in Example 1 were repeated except that commercially available methyl cellulose per se was substituted for the hydroxypropylmethyl cellulose used in Example 1. The results obtained are listed in Table 1 together with the particle size distribution of the cellulose.

It was found that the particulate samples of Examples 1 to 7 each could be dissolved in water within minutes, while the dissolution of the samples of Comparative Examples 1 to 4 required more than 30 minutes.

TABLE 1

|  | Examples | | | | | | | Comparative Examples | | | |
|---|---|---|---|---|---|---|---|---|---|---|---|
|  | 1 | 2 | 3 | 4 | 5 | 6 | 7 | 1 | 2 | 3 | 4 |
| Particle Size Distribution mesh ($\mu$m) | | | | | | | | | | | |
| 16 (1000) on | 1.0 | 0.6 | 0.4 | 1.0 | 1.8 | 0.6 | 2.8 | 0.4 | 0.4 | 0.8 | 3.8 |
| 24 (710) on | 18.5 | 4.4 | 14.0 | 4.5 | 1.2 | 6.9 | 20.2 | 4.6 | 4.9 | 7.6 | 8.3 |
| 30 (500) on | 42.5 | 29.8 | 37.4 | 11.0 | 9.5 | 42.9 | 49.0 | 9.5 | 10.4 | 14.6 | 13.4 |
| 42 (355) on | 18.5 | 25.2 | 20.6 | 16.2 | 29.8 | 29.8 | 21.2 | 16.5 | 11.6 | 14.2 | 14.3 |
| 60 (250) on | 7.0 | 14.8 | 7.0 | 17.9 | 25.5 | 11.5 | 4.8 | 20.2 | 24.4 | 22.8 | 37.6 |
| 83 (180) on | 3.8 | 6.8 | 4.6 | 15.6 | 12.5 | 4.3 | 1.5 | 32.5 | 22.2 | 16.8 | 13.6 |
| 83 (180) pass | 8.7 | 18.4 | 16.0 | 16.6 | 19.7 | 4.0 | 0.5 | 16.3 | 26.1 | 23.2 | 9.0 |
| Average Particle Size ($\mu$m) | 504 | 373 | 429 | 255 | 313 | 498 | 622 | 54 | 50 | 55 | 62 |
| Viscosity (cP)* | 3.0 | 6.0 | 15.0 | 15.0 | 6.0 | 6.0 | 6.0 | 3.0 | 6.0 | 15.0 | 15.0 |
| Dissolution Time (min) | 5 | 10 | 25 | 25 | 15 | 10 | 10 | 35 | 60 | 90 | 100 |

*Viscosity of a 2% aqueous solution as determined at 20° C.

What is claimed is:

1. A powdery starting material for preparing a drug-coating solution comprising hydroxypropylmethyl cellulose and/or methyl cellulose particles having an average particle size ranging from 200 to 1000 $\mu$m and whose content of particles having a particle size of 75 $\mu$m or smaller is not more than 30% by weight.

2. The powdery starting material for preparing a drug-coating solution according to claim 1 wherein the viscosity of a 2% by weight aqueous solution of the powdery starting material as determined at room temperature ranges from 2 to 60 cP.

3. The powdery starting material for preparing a drug-coating solution according to claim 1 wherein the particle size of the hydroxypropylmethyl cellulose and/or methyl cellulose particles is controlled by enlarging particles having a predetermined particle size starting from fine particles or a solution thereof.

4. The powdery starting material for preparing a drug-coating solution according to claim 3 wherein the particle-enlarging method is selected from the group consisting of stirred granulation methods, stirred fluidized bed granulation methods, fluidized bed granulation methods, spray dry methods and spray dry fluidized bed granulation methods.

5. The powdery starting material for preparing a drug-coating solution according to claim 1 wherein the particle size of the hydroxylpropylmethyl cellulose and/or methyl cellulose particles is controlled by pulverizing a massive body thereof and then classifying the resulting particles.

* * * * *